(12) United States Patent
Vik et al.

(10) Patent No.: US 11,901,058 B2
(45) Date of Patent: *Feb. 13, 2024

(54) ASSOCIATING AN INFORMATION READER AND A MEDICAL DEVICE

(71) Applicant: CareFusion 303, Inc., San Diego, CA (US)

(72) Inventors: Daniel Vik, Sunnyvale, CA (US); Sreelal Chandrasenan, San Diego, CA (US); Gregory Borges, San Diego, CA (US)

(73) Assignee: CareFusion 303, Inc., San Diego, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/109,202

(22) Filed: Feb. 13, 2023

(65) Prior Publication Data

US 2023/0360757 A1 Nov. 9, 2023

Related U.S. Application Data

(63) Continuation of application No. 16/570,604, filed on Sep. 13, 2019, now Pat. No. 11,581,078, which is a continuation of application No. 15/979,184, filed on May 14, 2018, now Pat. No. 10,418,130, which is a continuation of application No. 15/404,503, filed on
(Continued)

(51) Int. Cl.
| | |
|---|---|
| *G16H 20/17* | (2018.01) |
| *G16H 20/10* | (2018.01) |
| *G16H 40/63* | (2018.01) |
| *G16H 40/20* | (2018.01) |
| *G06F 16/955* | (2019.01) |
| *G16Z 99/00* | (2019.01) |
| *G06K 7/10* | (2006.01) |

(Continued)

(52) U.S. Cl.
CPC ......... *G16H 20/10* (2018.01); *G06F 16/9554* (2019.01); *G06K 7/10366* (2013.01); *G06K 7/1413* (2013.01); *G16H 40/20* (2018.01); *G16H 40/40* (2018.01); *G16H 40/63* (2018.01); *G16Z 99/00* (2019.02)

(58) Field of Classification Search
CPC ......... G16H 20/10; G16H 20/17; G16H 40/60
USPC .................. 235/462.13, 462.15, 462.01, 470
See application file for complete search history.

(56) References Cited

U.S. PATENT DOCUMENTS

| | | |
|---|---|---|
| 4,476,381 A | 10/1984 | Rubin |
| 7,813,822 B1 | 10/2010 | Hoffberg |

(Continued)

FOREIGN PATENT DOCUMENTS

| | | |
|---|---|---|
| JP | 2007-310759 A | 11/2007 |
| JP | 2011-065481 A | 3/2011 |

(Continued)

*Primary Examiner* — Paultep Savusdiphol
(74) *Attorney, Agent, or Firm* — Mintz Levin Cohn Ferris Glovsky and Popeo, P.C.

(57) ABSTRACT

A device agent including an information accessor for accessing association information obtained via an information reader. The association information includes medical device information for uniquely identifying the medical device, and device agent information for facilitating in an association between the medical device and the information reader. The device agent also includes an associator for associating the medical device and the information reader based on the association information.

18 Claims, 5 Drawing Sheets

Related U.S. Application Data

Jan. 12, 2017, now Pat. No. 9,996,676, which is a continuation of application No. 14/733,885, filed on Jun. 8, 2015, now Pat. No. 9,547,751, which is a continuation of application No. 13/275,005, filed on Oct. 17, 2011, now Pat. No. 9,053,520.

(51) Int. Cl.
*G06K 7/14* (2006.01)
*G16H 40/40* (2018.01)

(56) References Cited

U.S. PATENT DOCUMENTS

| | | | |
|---|---|---|---|
| 7,839,266 B2 | 11/2010 | Hoglund et al. | |
| 8,058,986 B2 | 11/2011 | Klabunde et al. | |
| 9,213,928 B2* | 12/2015 | Neff | G06K 17/0025 |
| 2002/0071076 A1 | 6/2002 | Webb et al. | |
| 2003/0135388 A1* | 7/2003 | Martucci | G06Q 10/087 |
| | | | 705/2 |
| 2003/0139701 A1* | 7/2003 | White | A61M 5/142 |
| | | | 604/67 |
| 2003/0140928 A1 | 7/2003 | Bui et al. | |
| 2003/0140929 A1 | 7/2003 | Wilkes et al. | |
| 2003/0141981 A1 | 7/2003 | Bui et al. | |
| 2003/0144878 A1 | 7/2003 | Wilkes et al. | |
| 2003/0173405 A1 | 9/2003 | Wilz et al. | |
| 2004/0019464 A1 | 1/2004 | Martucci et al. | |
| 2004/0104271 A1 | 6/2004 | Martucci et al. | |
| 2004/0167465 A1 | 8/2004 | Mihai et al. | |
| 2004/0167804 A1 | 8/2004 | Simpson et al. | |
| 2004/0172222 A1 | 9/2004 | Simpson et al. | |
| 2004/0172301 A1 | 9/2004 | Mihai et al. | |
| 2004/0172302 A1 | 9/2004 | Martucci et al. | |
| 2004/0176667 A1 | 9/2004 | Mihai et al. | |
| 2004/0193453 A1 | 9/2004 | Butterfield et al. | |
| 2004/0243434 A1 | 12/2004 | Peterka et al. | |
| 2005/0055242 A1 | 3/2005 | Bello et al. | |
| 2005/0055244 A1 | 3/2005 | Mullan et al. | |
| 2005/0065817 A1 | 3/2005 | Mihai et al. | |
| 2005/0108057 A1 | 5/2005 | Cohen et al. | |
| 2005/0140498 A1 | 6/2005 | Bastian, II | |
| 2005/0149350 A1 | 7/2005 | Kerr et al. | |
| 2005/0182661 A1 | 8/2005 | Allard et al. | |
| 2005/0267402 A1 | 12/2005 | Stewart et al. | |
| 2006/0229557 A1* | 10/2006 | Fathallah | G16H 40/63 |
| | | | 705/2 |
| 2007/0145137 A1 | 6/2007 | Mrowiec | |
| 2007/0267475 A1 | 11/2007 | Hoglund et al. | |
| 2007/0300063 A1 | 12/2007 | Adams et al. | |
| 2008/0071251 A1 | 3/2008 | Moubayed et al. | |
| 2008/0148040 A1 | 6/2008 | Machani et al. | |
| 2008/0149701 A1 | 6/2008 | Lane | |
| 2008/0221930 A1 | 9/2008 | Wekell et al. | |
| 2008/0275422 A1 | 11/2008 | Ross | |
| 2008/0303638 A1 | 12/2008 | Nguyen et al. | |
| 2009/0231124 A1 | 9/2009 | Klabunde et al. | |
| 2010/0169120 A1 | 7/2010 | Herbst et al. | |
| 2010/0292645 A1 | 11/2010 | Hungerford et al. | |
| 2011/0238032 A1 | 9/2011 | McTaggart et al. | |
| 2012/0179130 A1 | 7/2012 | Barnes et al. | |

FOREIGN PATENT DOCUMENTS

| | | |
|---|---|---|
| KR | 10-2004-0073560 | 8/2004 |
| WO | WO-00/16211 A1 | 3/2000 |
| WO | WO-03/060805 A2 | 7/2003 |

* cited by examiner

500

```
ACCESS ASSOCIATION INFORMATION VIA THE INFORMATION READER,
WHEREIN THE INFORMATION COMPRISES: MEDICAL DEVICE INFORMATION
FOR UNIQUELY IDENTIFYING THE MEDICAL DEVICE; AND DEVICE AGENT
INFORMATION FOR FACILITATING IN AN ASSOCIATION BETWEEN THE
MEDICAL DEVICE AND THE INFORMATION READER
510
```

```
ACCESS ASSOCIATION INFORMATION DISPLAYED PROXIMATE THE
MEDICAL DEVICE
512
```

```
ASSOCIATE THE MEDICAL DEVICE AND THE INFORMATION READER BASED ON
THE ASSOCIATION INFORMATION
520
```

```
ESTIMATE A PROXIMITY BETWEEN THE MEDICAL DEVICE AND THE
INFORMATION READER
530
```

```
ROUTE SUBSEQUENT INFORMATION OBTAINED VIA THE INFORMATION READER
TO THE MEDICAL DEVICE
540
```

```
ROUTE SUBSEQUENT INFORMATION OBTAINED VIA THE INFORMATION READER
TO ANOTHER MEDICAL DEVICE, WHEREIN THE ANOTHER MEDICAL DEVICE IS
ASSOCIATED WITH THE MEDICAL DEVICE
550
```

```
IN RESPONSE TO THE ASSOCIATION, ROUTE PREVIOUSLY OBTAINED
INFORMATION TO THE MEDICAL DEVICE
560
```

```
DISASSOCIATE THE ASSOCIATION BETWEEN THE MEDICAL DEVICE AND THE
INFORMATION READER
570
```

FIG. 5

ASSOCIATING AN INFORMATION READER AND A MEDICAL DEVICE

CROSS REFERENCE TO RELATED APPLICATIONS

This application is a continuation of U.S. patent application Ser. No. 15/979,184, filed May 14, 2018, which is a continuation of U.S. patent application Ser. No. 15/404,503 (now issued as U.S. Pat. No. 9,996,676), filed Jan. 12, 2017, which is a continuation of U.S. patent application Ser. No. 14/733,885 (now issued as U.S. Pat. No. 9,547,751), filed Jun. 8, 2015, which is a continuation of U.S. patent application Ser. No. 13/275,005 (now issued as U.S. Pat. No. 9,053,520), filed Oct. 17, 2011, each entitled "Associating An Information Reader and A Medical Device", the contents of which are herein incorporated by reference in their entirety.

BACKGROUND

Barcode systems are often used in medical environments to ensure safety. For example, a barcode system can ensure that correct drugs are given to the proper patient or only authorized personnel can administer the proper medical protocol to a patient.

Oftentimes, a barcode scanner is permanently associated with a single medical device. For example, the barcode scanner is physically attached to the medical device. As a result, the flexibility of a medical environment is limited because it is difficult to share barcode scanners with other medical devices.

Also, a floating barcode is utilized in BCMA systems. For floating barcode devices, barcode scans are sent to a centralized system. The scanning is only done to get information (e.g., device id, similar to when you scan a badge), and the information is used in backend systems to perform some general work. However, the intent and workflow, regarding the floating barcode in a BCMA system, is not for directing subsequent barcode scans to a particular device.

Moreover, a barcode scanner may be unable to directly communicate with a medical device because of limited communication capabilities.

BRIEF DESCRIPTION OF THE DRAWINGS

FIG. 5 illustrates an embodiment a method for associating an information reader and medical device.

The drawings referred to in this description should be understood as not being drawn to scale except if specifically noted.

DESCRIPTION OF EMBODIMENTS

Reference will now be made in detail to embodiments of the present technology, examples of which are illustrated in the accompanying drawings. While the technology will be described in conjunction with various embodiment(s), it will be understood that they are not intended to limit the present technology to these embodiments. On the contrary, the present technology is intended to cover alternatives, modifications and equivalents, which may be included within the spirit and scope of the various embodiments as defined by the appended claims.

Furthermore, in the following description of embodiments, numerous specific details are set forth in order to provide a thorough understanding of the present technology. However, the present technology may be practiced without these specific details. In other instances, well known methods, procedures, components, and circuits have not been described in detail as not to unnecessarily obscure aspects of the present embodiments.

In general, information readers are associated with medical devices to ensure safety in a medical environment. The discussion below will describe a variety of means to associate an information reader with medical device(s). In particular, the discussion will first describe the components in a medical environment. Then the discussion will describe functionality of the components during use of the medical environment.

It is understood that "association," as used herein, for example, the association between an information reader and a medical device, generally describes the communicative coupling between the devices. As a result of the association, information, obtained by the information reader, is able to be routed to the associated device(s).

Figure 1:
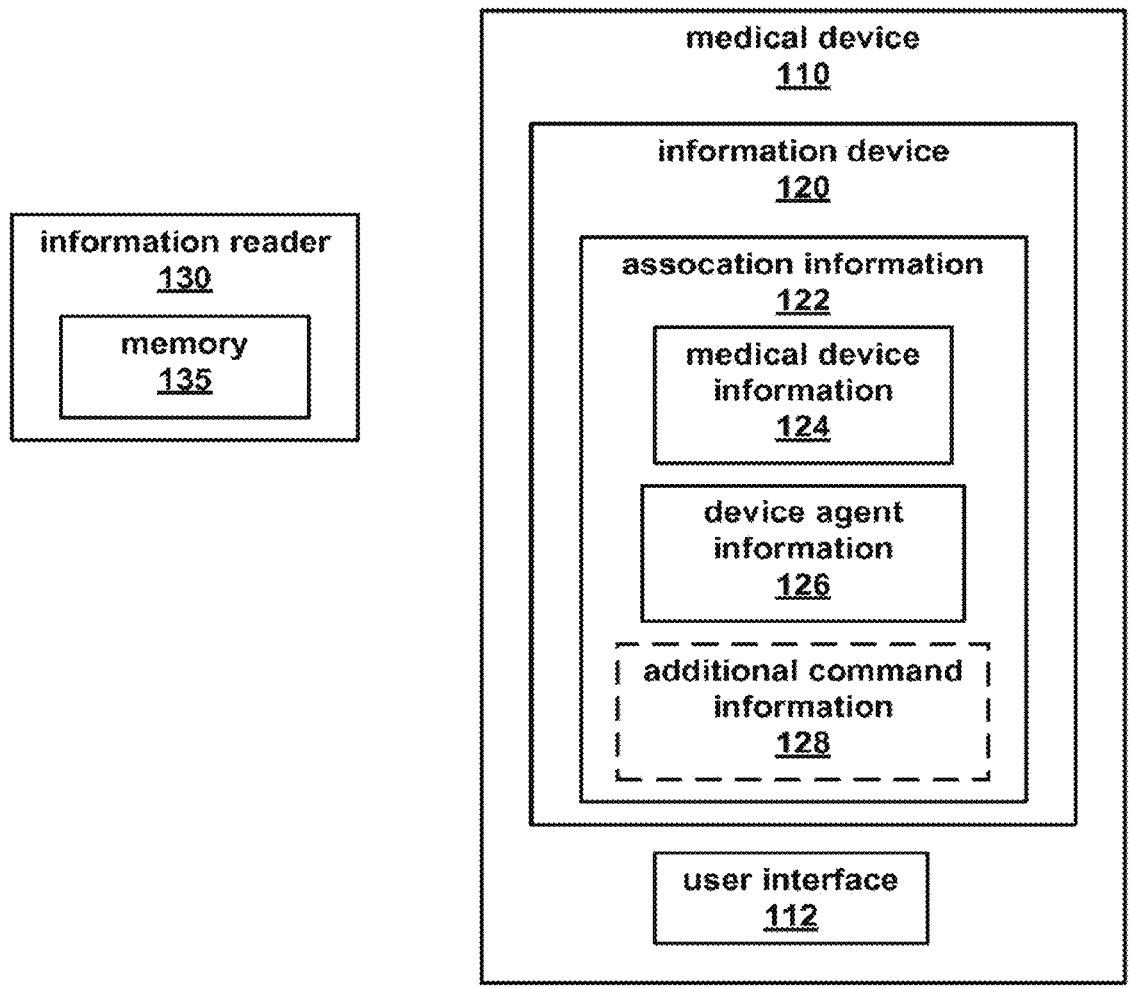
FIGS. 1-3 illustrate embodiments of a medical system.

FIG. 1 depicts an embodiment of medical environment 100. Medical environment 100 includes medical device 110, information reader 130 and device agent 140.

Information reader 130 is any device that is capable of reading information and also able to be associated with a medical device. For example, information reader 130 can be, but is not limited to, a barcode scanner, a radio-frequency identification (RFID) reader. Moreover, information reader 130 can be any device (e.g., a mobile device) with barcode scanning and/or RFID reading capabilities.

Medical device 110 can be any medical device(s) that is able to be associated with an information reader. For example, medical device is a ventilator, infusion pump, etc.

In general, association information 122 is utilized to facilitate in the association between information reader 130 and medical device 110. Association information 122 includes medical device information 124, device agent information 126 and optionally, additional command information 128.

Also, in various embodiments, association information 122 includes a cookie (data element) that appends to any consecutive scan after an association generated. The cookie allows the destination device (and/or routing devices) to uniquely identify scans intended for the destination device.

Medical device information 124 includes any information or signature that uniquely identifies medical device 110 and/or any other medical devices. For example, medical device information 124 can be, but is not limited to, model number, serial number, Media Access Control address (MAC) address, Internet Protocol (IP) address, etc.

Device agent information 126 includes any information that can be utilized by device agent 140 (or any other device agent) to properly route information, obtained by information reader 130, to medical device 110. For example, device agent information 126 can include, but is not limited to, agent name, connectivity parameters (e.g., IP/Bluetooth parameters), commands for routing information to a specific device (e.g., medical device 110), and authentication information.

Additional command information 128 can be any additional information (other than medical device information 124 and device agent information 126) that provides commands for routing information obtained by information reader 130. For example, additional command information 128 can provide commands to device agent 140 to route information to other devices. In another example, command information 128 can include disassociation information (e.g., disassociate immediately, or after X seconds).

Association information 122 is able to be read or obtained by information reader 130 via information device 120. In various embodiments, information device 120 is a barcode (static or dynamic) or an RFID tag. Accordingly, association information 122 is presented as a static barcode, a dynamic barcode or an RFID tag. As such, information reader 130 (e.g., a barcode reader or an RFID reader) is able to read or obtain association information 122 via information device 120.

In one embodiment, information device 120 is attached to medical device 110. For instance, a barcode or an RFID tag is physically attached (e.g., adhered) to an infusion pump.

In another embodiment, information device 120 is a display for rendering a scannable barcode. In such an embodiment, association information 122 is dynamically displayed on information device 120. Also, the display can be integrated within medical device 110 or can be separate, but proximate to, medical device 110. It should be understood that the rendered barcode (displayed on the display) contains the association information 122 describe above.

Device agent 140 is an agent or proxy for medical device 110 and is utilized to facilitate in the association between information reader 130 and medical device 110. Device agent 140 includes information accessor 142, router 144, associator 146, disassociator 148, and optionally, proximity estimator 149.

Information accessor 142 is for accessing association information 122 via information reader 130.

Associator 146 is configured for associating medical device 110 and information reader 130 based on association information 122. Disassociator 148 is for disassociating an established association between information reader 130 and medical device 110.

Proximity estimator 146 is for estimating a proximity or distance between medical device 110 and information reader 130.

Router 144 is for routing subsequent information (e.g., information from a scanned barcode on a bottle of medicine) to medical device 110.

During use of medical environment 100, information reader 130 and medical device 110 are initially unassociated. As such, any information obtained by information reader 130 would not necessarily be routed to medical device 110.

In order to associate information reader 130 and medical device 110, information reader 130 reads association information 122. In particular, medical device information 124 and device agent information 126. For example, a handheld barcode scanner scans a barcode that includes the serial number of medical device 110 and the MAC address for device agent 140.

Information reader 130 communicates with device agent 140 in a variety of ways. In various examples, information reader 130 communicates with device agent 140 by Universal Serial Bus (USB), internet, Wi-Fi, Bluetooth, etc.

Information accessor 142 accesses association information 122. Associator 150 obtains association information 122 and associates information reader 130 and medical device 110 based on association information 122. For example, associator 150 generates an association based on the received serial number of medical device 110 and the MAC address for device agent 140.

In one embodiment, associator 146 automatically generates an association in response to the obtained association information 122. In another embodiment, associator 146 automatically generates an association in response to user input, which will be described in detail below.

As a result of the generated association, router 144 routes subsequent information obtained by information reader 130 to medical device 110. For example, batches of medication are intended to be infused into Patient A. Barcodes on the batches of medication are scanned by information reader 130. The information from the scanned barcodes are then routed to medical device 110 (e.g., an infusion pump) to facilitate in the infusion of the drugs into Patient A.

In one embodiment, information reader 130 obtains information prior to an established association with medical device 110. For example, information reader 130 obtains information by scanning barcodes on batches of medicine for Patient A. The information is stored in memory 135. Memory 135 can be located within information reader 130 or other locations, such as a server, within medical environment 100.

In response to an association between information reader 130 and medical device 110 (established by associator 146), the information (obtained prior to association) stored in memory 135 is routed to medical device 110.

In various embodiments, the association is a logical peer-to-peer association between information reader 130 and medical device 110. FIG. 1 depicts an association through device agent 140. However, in various other embodiments, the association can utilize point-to-point radio technology on a network (e.g., a local area network (LAN), a wireless LAN (WLAN), or a personal area network (PAN) (e.g., Bluetooth or Zigbee)). In an embodiment of a PAN, direct communication between information reader 130 and medical device 110 is established without requiring any network infrastructure.

Figure 4:
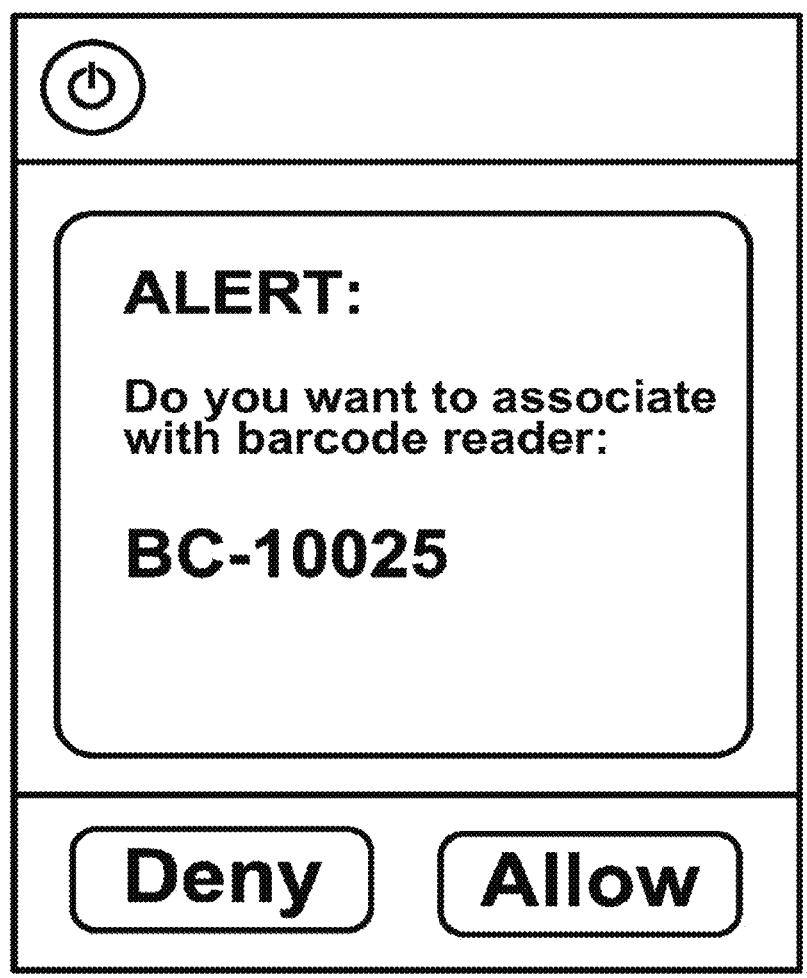
FIG. 4 illustrates an embodiment of displayed information.

Referring now to FIG. 4, to enhance safety and control (enabled or disabled through device configuration) an acknowledgment dialog 400 is displayed on user interface 112 of medical device 110.

A user is prompted to accept the attempted association. If the user chooses to deny the association attempt, medical device 110 will not accept subsequent information (e.g., subsequent barcode scans) from information reader 130, unless a new authentication is performed and accepted.

Referring again to FIG. 1, disassociator 148 terminates or disassociates the association between information reader 130 and medical device 110. In order to reduce the likelihood of undesired information to be routed to a medical device, provisions are added to limit the duration that the association is effective.

For example, a disassociation of an information reader from a medical device can be accomplished via a user interface of the information reader and/or medical device.

Disassociation can automatically occur after a pre-determined amount of time from association. For example, a disassociation automatically occurs after four hour from the time of association.

Disassociation can occur after a pre-determined amount of time from the last scan. For example, a disassociation automatically occurs after one hour from the last scan of the information reader.

Disassociation can occur in response to the devices exceeding a pre-determined maximum distance. For example, proximity estimator 149 estimates the proximity between information reader 130 and medical device 110. In response to medical device 110 and information reader 130 exceeding a pre-determined maximum distance (e.g., 40 feet), medical device 110 and information reader 130 are disassociated.

Disassociation can automatically occur in response if a connection (e.g., wireless) between the devices is lost.

Disassociation can automatically occur in response to completed work flow. For example, disassociation occurs after successful drug scanning, and patient ID and/or clinician ID are associated with the medical device.

Disassociation can occur if information reader reads/obtains association information of another medical device.

Figure 2:
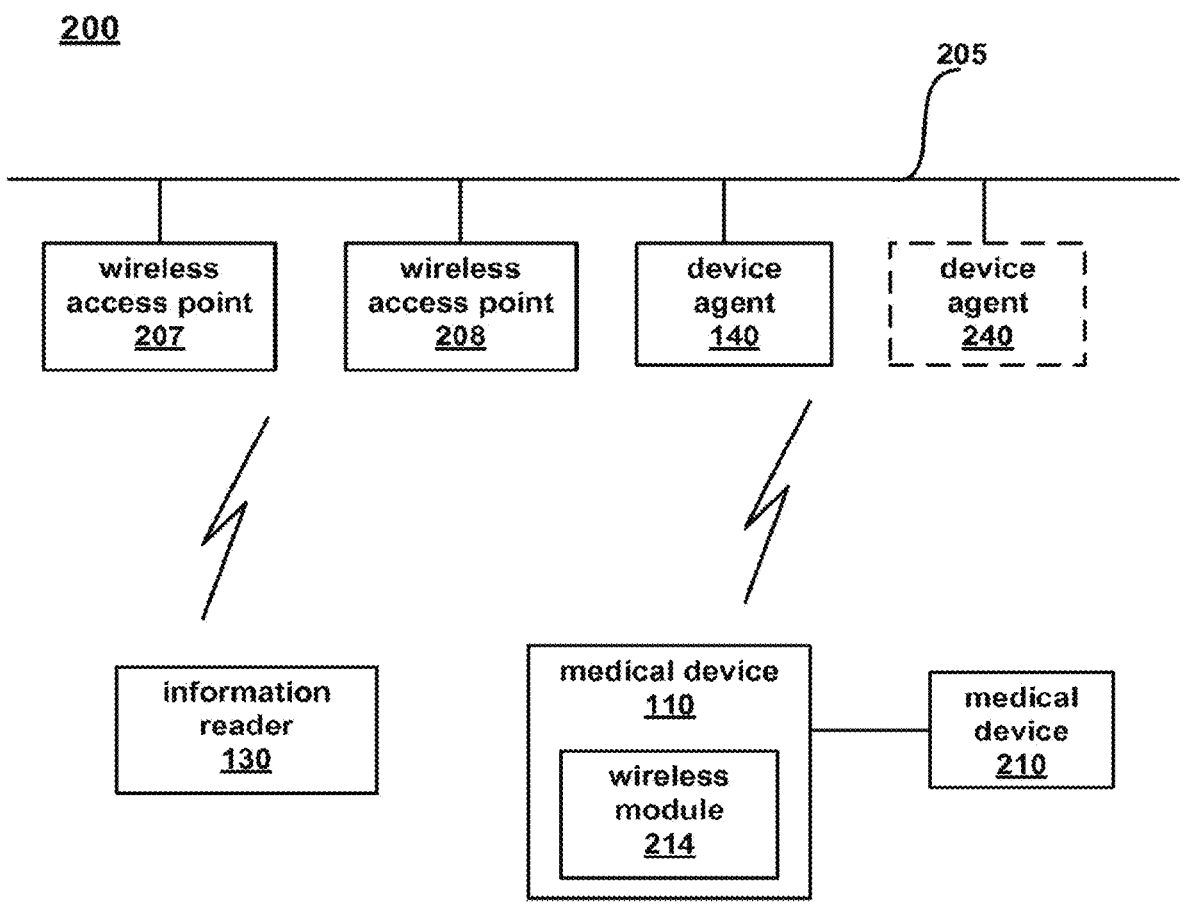

Referring to FIG. 2, medical environment 200 includes network 205, wireless access points 207 and 208, device agents 140 and 240, information reader 130, and medical devices 110 and 210.

Medical device 110 also includes wireless module 214. Wireless module 214 allows for medical device 110 to wirelessly connect to network 205 via wireless access points 207 and/or 208.

Also, medical device 110 is connected to or associated with other medical devices, such as medical device 210. For example, medical device 110 is a first Large Volume Parenterals (LVP) device and medical device 210 is a second LVP device.

Moreover, medical device 210 does not have the capability to directly communicate with information reader 130. Although two medical devices are depicted in FIG. 2, it should be appreciated that any number of medical devices can be connected to or associated with one another.

During use of medical environment 200, information reader 130 can be associated with medical device 110 in the same manner as described above.

In one embodiment, information 130 can also be associated with medical device 210. In order to associate information reader 130 and medical device 210, information reader 130 reads association information 122 which is presented by medical device 110. In particular, information reader 130 reads medical device information 124 which uniquely identifies medical device 210.

Information accessor 142 accesses association information 122. Associator 150 obtains association information 122 and subsequently associates information reader 130 and medical device 210 based on association information 122. As a result of the generated association, router 144 routes subsequent information obtained by information reader 130 to medical device 210.

It should be appreciated that information reader 130 can be concurrently associated with medical devices 110 and 210.

It may be desired that medical devices 110 and 210 are to utilize device agent 240 rather than device agent 140. For example, medical devices 110 and 210 initially utilize device agent 140. However, for purposes of testing the medical devices, device agent 240 (e.g., a testing device agent) is utilized.

Accordingly, information reader 130 reads association information 122. In particular, information reader 130 reads device agent information 126 which identifies device agent 240. As a result, subsequent information obtained by information reader 130 is routed to medical device 110 and/or 210 via router 240 (rather than device agent 140).

A device agent (e.g., device agent 140) can optionally add functionality to the system. The device agent can be a physical device or virtual device agent, which has close communication with the medical devices. The device agent can manage the scan workflows and rules such as valid scan, valid sequence of scans, association and disassociation of barcode. A valid scan can include valid data in the scan, a scan supported by a medical device such as intermittent infusion or PCA infusion not supported by the device. A valid sequence may include scanning patient ID, clinical ID and a drug scan.

A device agent can determine when to associate the barcode and when to disassociate the barcode. A device agent may perform preprocessing of the scan before sending to medical device such as mapping the drug entry ID to drug name or order ID to order details. In this case, the device agent will store drug library and order information.

Figure 3:
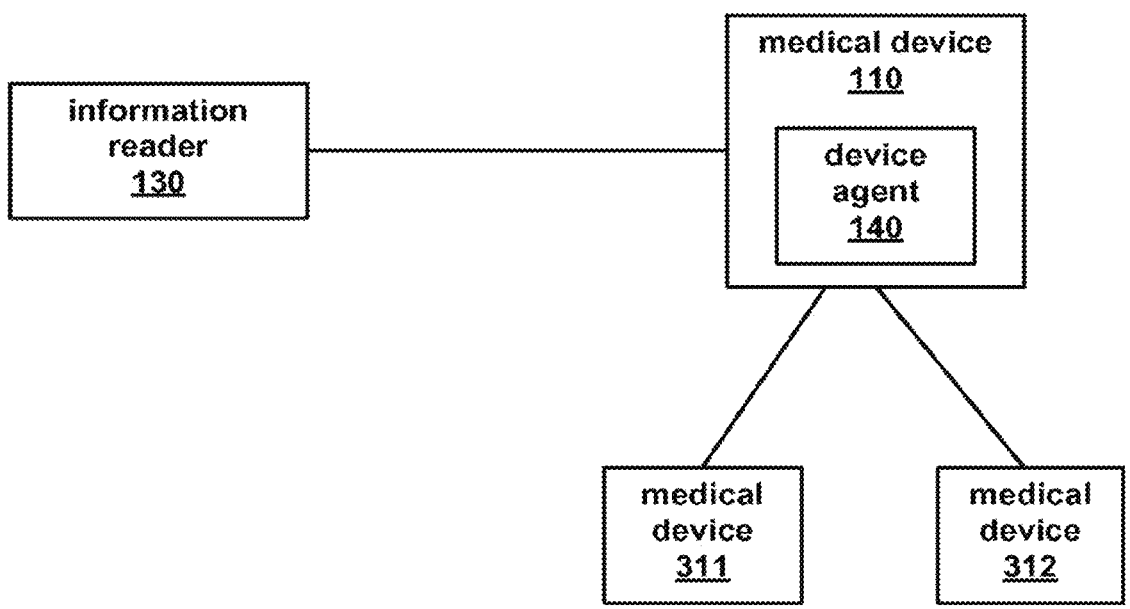

Referring to FIG. 3, an embodiment of medical environment 300 is depicted. Medical environment 300 includes information reader 130 and medical devices 110, 310 and 312.

In such an embodiment, medical device 110 includes device agent 140. In other words, medical device 110 also functions as device agent 140. For example, medical device 110, 310 and 312 are devices in a medical device rack system. As such, medical device 110 acts as a proxy or device agent for medical devices 311 and 312 because medical devices 311 and 312 do not have the capability to directly communicate with information reader 130.

During use of medical environment 300, information reader 130 can be associated with medical device 310 in the same manner as described above.

In another embodiment, information 130 can also be associated with medical devices 311 and 312. In order to associate information reader 130 and medical devices 311 and/or 312, information reader 130 reads association information 122 which is presented by medical device 310. In particular, information reader 130 reads medical device information 124 which uniquely identifies medical devices 311 and/or 312.

Information accessor 142 accesses association information 122. Associator 150 obtains association information 122 and subsequently associates information reader 130 and medical devices 311 and/or 312 based on association information 122. As a result of the generated association, router 144 routes subsequent information obtained by information reader 130 to medical devices 311 and/or 312.

FIG. 5 depicts an embodiment of a method 500 for associating an information reader and a medical device. In various embodiments, method 500 is carried out by processors and electrical components under the control of computer readable and computer executable instructions. The computer readable and computer executable instructions reside, for example, in a data storage medium such as computer usable volatile and non-volatile memory. However, the computer readable and computer executable instructions may reside in any type of computer readable storage medium. In some embodiments, method 500 is performed at least by device agent 140 and/or medical device 110, as depicted in FIG. 1.

At 510 of method 500, association information is accessed via the information reader, wherein the information comprises medical device information for uniquely identifying the medical device, and device agent information for facilitating in an association between the medical device and the information reader.

For example, association information 122 is scanned by information reader 130 (e.g., barcode scanner). In particular, association information 122 includes medical device information 124 which is a unique signature of medical device 110 and device agent information 126 which can include agent name, connectivity parameters (e.g., IP/Bluetooth parameters), and/or commands for routing information to a specific device.

In one embodiment, at 512, association information displayed proximate the medical device is accessed. For example, association information 122 is presented by information device 120 (e.g., dynamic barcode) which is physically attached to medical device 110.

At 520, the medical device and the information reader are associated based on the association information. For example, associator 146 associates information reader 130 and medical device 110 based on association information 122.

At 530, a proximity is estimated between the medical device and the information reader. For example, information reader 130 and medical device 110 are disassociated in response to the devices exceeding a maximum distance. It should be understood that the proximity estimation utilized for disassociation is just one embodiment for managing disassociation. In particular, the proximity estimation is not required in all embodiments.

At 540, subsequent information obtained via the information reader is routed to the medical device. For example, router 144 routes information obtained by scanning barcodes on batches of medicine to medical device 110.

At 550, subsequent information obtained via the information reader is routed to another medical device, wherein the another medical device is associated with the medical device. For example, router 144 routes information obtained by scanning barcodes on batches of medicine to medical devices 311 and/or 312.

At 560, in response to the association, route previously obtained information to the medical device. For example, prior to association, information reader 130 obtains information and the information is stored in memory 135. In response associator 146 establishing an association between information reader 130 and medical device 110, the information stored in memory 135 is routed to medical device 110.

At 570, a disassociation occurs between the medical device and the information reader. For example, disassociation occurs in response to a lost wireless connection between medical device 110 and information reader 130.

Various embodiments of the present invention are thus described. While the present invention has been described in particular embodiments, it should be appreciated that the present invention should not be construed as limited by such embodiments, but rather construed according to the following claims.

The invention claimed is:

1. An infusion pump for infusion within a medical environment, the infusion pump comprising:
a display;
a wireless module configured to communicate with a wireless network;
at least one data processor; and
at least one memory including computer program code, the at least one memory and the computer program code configured to, with the at least one data processor, cause the infusion pump to at least:
render a barcode on the display of the infusion pump, wherein the barcode is configured to be scanned by a barcode reader;
configure the infusion pump for receiving infusion information;
receive, via the wireless module, infusion information about an infusion to be administered to a patient after the barcode reader scans the barcode on the display of the infusion pump and an infusion barcode on the infusion to be administered, the infusion information including at least one of an infusion parameter of the infusion to be administered, an infusion name, or an infusion order identifier; and
operate, based at least on the received infusion information, to cause administration of the infusion.

2. The infusion pump of claim 1, wherein the at least one memory and the computer program code are further configured to, with the at least one data processor, cause the infusion pump to receive patient information identifying the patient after the barcode reader scans a patient identifier.

3. The infusion pump of claim 1, wherein the at least one memory and the computer program code are further configured to, with the at least one data processor, cause the infusion pump to receive clinical information identifying a clinician after the barcode reader scans a clinician identifier.

4. The infusion pump of claim 1, wherein the at least one memory and the computer program code are further configured to, with the at least one data processor, cause the infusion pump to:
store the infusion information in the at least one memory of the infusion pump; and
render, on the display, at least a portion of the infusion information.

5. The infusion pump of claim 1, wherein the barcode further comprises routing information defining parameters for routing the infusion information to the infusion pump.

6. The infusion pump of claim 5, wherein the routing information comprises at least one of: a connectivity parameter of the infusion pump or authentication information of the infusion pump.

7. The infusion pump of claim 1, wherein the infusion to be administered to the patient is a medication.

8. An infusion system for infusion within a medical environment, the infusion system comprising:
a display;
a wireless module configured to communicate with a wireless network;
at least one data processor; and
at least one memory including computer program code, the at least one memory and the computer program code configured to, with the at least one data processor, cause the infusion system to at least:
render a barcode on the display, wherein the barcode is configured to be scanned by a barcode reader;
receive infusion information about an infusion to be administered to the patient after the barcode reader scans the barcode on the display and an infusion barcode on the medication, the infusion information including at least one of an infusion parameter of the infusion, an infusion name, or an infusion order identifier; and
cause, based at least on the received infusion information, administration of the infusion.

9. The infusion system of claim 8,
wherein the barcode comprises routing information defining a parameter for routing the infusion information to the infusion system.

10. The infusion system of claim 8, wherein the at least one memory and the computer program code are further configured to, with the at least one data processor, cause the infusion pump to:
store the infusion information in the at least one memory; and
render, on the display, at least a portion of the infusion information.

11. The infusion system of claim 8, wherein the at least one memory and the computer program code are further configured to, with the at least one data processor, cause the infusion system to receive second infusion information about a second infusion to be administered to the patient by the infusion system, the second infusion information including at least one of: an infusion parameter of the second infusion, a second infusion name, or a second infusion order identifier.

12. The infusion system of claim 8, wherein the at least one memory and the computer program code are further configured to, with the at least one data processor, cause the infusion system to:
receive at least one of patient information identifying a patient or clinician information identifying a clinician after the barcode reader scans the at least one of the patient information or the clinician information.

13. An infusion pump for infusion within a medical environment, the infusion pump comprising:
a display;
a wireless module configured to communicate with a wireless network;
at least one data processor; and
at least one memory including computer program code, the at least one memory and the computer program code configured to, with the at least one data processor, cause the infusion pump to at least:
render a barcode on the display of the infusion pump, wherein the barcode is configured to be scanned by a mobile device;
configure the infusion pump for receiving infusion information;
receive, via the wireless module, infusion information about an infusion to be administered to a patient after the mobile device scans the barcode on the display of the infusion pump and an infusion barcode on the infusion to be administered, the infusion information including at least one of an infusion parameter of the infusion to be administered, an infusion name, or an infusion order identifier; and
operate, based at least on the received infusion information, to cause administration of the infusion.

14. The infusion pump of claim 13, wherein the at least one memory and the computer program code are further configured to, with the at least one data processor, cause the infusion pump to receive patient information identifying the patient after the mobile device scans a patient identifier.

15. The infusion pump of claim 13, wherein the at least one memory and the computer program code are further configured to, with the at least one data processor, cause the infusion pump to receive clinical information identifying a clinician after the mobile device scans a clinician identifier.

16. The infusion pump of claim 13, wherein the at least one memory and the computer program code are further configured to, with the at least one data processor, cause the infusion pump to:
store the infusion information in the at least one memory of the infusion pump; and
render, on the display, at least a portion of the infusion information.

17. The infusion pump of claim 13, wherein the barcode further comprises routing information defining parameters for routing the infusion information to the infusion pump.

18. The infusion pump of claim 17, wherein the routing information comprises at least one of: a connectivity parameter of the infusion pump or authentication information of the infusion pump.

* * * * *